(12) United States Patent
Nakanishi et al.

(10) Patent No.: US 10,383,517 B2
(45) Date of Patent: Aug. 20, 2019

(54) OPHTHALMIC OPERATION MICROSCOPE

(71) Applicant: KABUSHIKI KAISHA TOPCON, Itabashi-ku (JP)

(72) Inventors: Michiko Nakanishi, Katsushika (JP); Ikuo Ishinabe, Saitama (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 7 days.

(21) Appl. No.: 15/549,213

(22) PCT Filed: Feb. 3, 2016

(86) PCT No.: PCT/JP2016/053281
§ 371 (c)(1),
(2) Date: Aug. 7, 2017

(87) PCT Pub. No.: WO2016/170817
PCT Pub. Date: Oct. 27, 2016

(65) Prior Publication Data
US 2018/0035887 A1 Feb. 8, 2018

(30) Foreign Application Priority Data

Apr. 20, 2015 (JP) ................. 2015-086136

(51) Int. Cl.
*A61B 3/10* (2006.01)
*A61B 3/13* (2006.01)
(Continued)

(52) U.S. Cl.
CPC .............. *A61B 3/13* (2013.01); *A61B 3/102* (2013.01); *A61B 90/20* (2016.02); *A61F 9/007* (2013.01);
(Continued)

(58) Field of Classification Search
CPC ......... A61B 3/13; A61B 90/20; A61B 3/1015; A61B 3/1225; A61B 3/1233;
(Continued)

(56) References Cited

U.S. PATENT DOCUMENTS 4,807,989 A * 2/1989 Nagano .................. A61F 9/013
351/206
7,978,404 B2 7/2011 Reimer et al.
(Continued)

FOREIGN PATENT DOCUMENTS

CN 103892919 A 7/2014
JP 2008-264489 A 11/2008
(Continued)

OTHER PUBLICATIONS

International Search Report dated Apr. 5, 2016; in PCT/JP2016/053281, filed Feb. 3, 2016.
(Continued)

*Primary Examiner* — William R Alexander
*Assistant Examiner* — Henry A Duong
(74) *Attorney, Agent, or Firm* — Xsensus LLP

(57) ABSTRACT

In an ophthalmic operation microscope, an illumination optical system illuminates a patient's eye with illumination light. An observation optical system is used for observing the patient's eye illuminated. An objective lens is disposed in an observation optical path. An interference optical system splits light from a light source into measurement light and reference light, and detects interference light generated from returning light of the measurement light from the patient's eye and the reference light. A first lens group is disposed between the light source and the patient's eye in an optical path of the measurement light. A second lens group is disposed between the first lens group and the patient's eye in the optical path of the measurement light. A deflection member is disposed between the first lens group and the second lens group in the optical path of the measurement light.

10 Claims, 5 Drawing Sheets

(51) Int. Cl.
    *A61F 9/007*     (2006.01)
    *G02B 21/22*     (2006.01)
    *A61B 90/20*     (2016.01)
    *G02B 21/00*     (2006.01)
    *A61F 9/008*     (2006.01)

(52) U.S. Cl.
    CPC ......... *G02B 21/0056* (2013.01); *G02B 21/22* (2013.01); *A61B 3/1015* (2013.01); *A61F 9/008* (2013.01)

(58) Field of Classification Search
    CPC ....... A61B 3/1241; A61B 3/102; A61F 9/007; A61F 9/008; G02B 21/22; G02B 21/0056
    USPC ......................................................... 351/221
    See application file for complete search history.

(56) References Cited

U.S. PATENT DOCUMENTS

| | | | |
|---|---|---|---|
| 8,049,873 | B2 | 11/2011 | Hauger et al. |
| 2008/0117432 | A1 | 5/2008 | Reimer et al. |
| 2008/0117503 | A1 | 5/2008 | Reimer et al. |
| 2008/0304144 | A1 | 12/2008 | Reimer et al. |
| 2010/0309478 | A1 | 12/2010 | Reimer et al. |
| 2011/0228218 | A1* | 9/2011 | Hauger .................. A61B 3/102 351/205 |
| 2012/0033181 | A1* | 2/2012 | Koizumi ................ A61B 3/102 351/208 |
| 2014/0055749 | A1* | 2/2014 | Zhou .................... A61B 3/0025 351/214 |
| 2014/0063505 | A1 | 3/2014 | Bajraszewski et al. |
| 2015/0313461 | A1 | 11/2015 | Bajraszewski et al. |

FOREIGN PATENT DOCUMENTS

| | | |
|---|---|---|
| JP | 2008-268852 A | 11/2008 |
| JP | 2013-52257 A | 3/2013 |
| JP | 2014-45908 A | 3/2014 |
| JP | 2014-64946 A | 4/2014 |
| JP | 2014-523537 A | 9/2014 |
| WO | 2014/074573 A1 | 5/2014 |

OTHER PUBLICATIONS

Notification of Reasons for Refusal issued in Japanese Application 2015-086136 dated Apr. 2, 2019.

* cited by examiner

OPHTHALMIC OPERATION MICROSCOPE

FIELD

Embodiments described herein relate generally to an ophthalmic operation microscope.

BACKGROUND ART

In the field of ophthalmology, various operations are carried out. Typical examples thereof include cataract surgery and vitreoretinal surgery. In such surgery in the field of ophthalmology, an ophthalmic operation microscope is used. The ophthalmic operation microscope is an apparatus for visually observing and imaging the patient's eye illuminated by the illumination optical system via the observation optical system.

An ophthalmic operation microscope including an optical coherence tomography (hereinafter referred to as OCT) optical system for acquiring an OCT image of a patient's eye using OCT (for example, refer to Patent Document 1).
[Patent Document 1] U.S. Pat. No. 8,049,873

However, in the ophthalmic operation microscope disclosed in Patent Document 1, the optical system is configured so that the OCT measurement light is deflected by the beam scanner, passes through the two lens groups, and then is reflected by the reflector toward the objective lens. Therefore, the optical system for guiding the OCT measurement light to the patient's eye is provided in a manner that it protrudes sideways from the main body of the microscope. This leads to an increase in the size of the ophthalmic operation microscope.

SUMMARY

The present invention is made for solving the aforementioned problem, and the object thereof is to provide a technique that enables miniaturization of an ophthalmic operation microscope for observing a patient's eye and acquiring an OCT image.

An ophthalmic operation microscope according to an embodiment includes an illumination optical system, an observation optical system, an objective lens, an interference optical system, a first lens group, a second lens group, and a deflection member. The illumination optical system illuminates a patient's eye with illumination light. The observation optical system is used for observing the patient's eye illuminated by the illumination optical system. The objective lens is disposed in an observation optical path. The interference optical system splits light from a light source into measurement light and reference light, and detects interference light generated from returning light of the measurement light from the patient's eye and the reference light. The first lens group is disposed between the light source and the patient's eye in an optical path of the measurement light. The second lens group is disposed between the first lens group and the patient's eye in the optical path of the measurement light. The deflection member is disposed between the first lens group and the second lens group in the optical path of the measurement light.

According to the embodiment, it is possible to miniaturize an ophthalmic operation microscope for observing a patient's eye and acquiring an OCT image.

DETAILED DESCRIPTION

Figure 1:
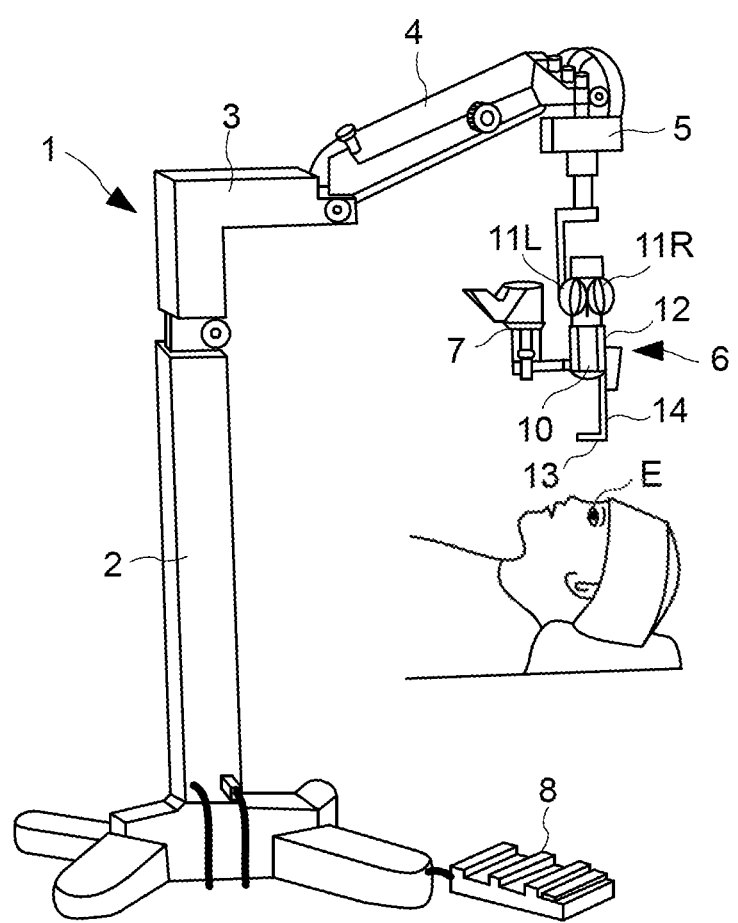
FIG. 1 is a schematic diagram illustrating an example of the exterior structure of an ophthalmic operation microscope according to an embodiment.

An exemplary embodiment of the ophthalmic operation microscope according to the present invention will be described in detail with reference to the drawings. The ophthalmic operation microscope according to the embodiment described below is used in ophthalmic surgery. The ophthalmic operation microscope according to the embodiment is an apparatus capable of observing a patient's eye by illuminating the patient's eye (eye to be operated) with an illumination optical system and guiding the returning light (reflected light) of the illumination to an observation optical system.

Further, the ophthalmic operation microscope according to the embodiment includes an OCT optical system, and is capable of acquiring OCT images of the patient's eye. The imaging target site may be an arbitrary site of the patient's eye. For example, the imaging target site may be a cornea, a vitreous body, a crystalline lens, a ciliary body, or the like in the anterior segment. In addition, the imaging target site may be a retina, a choroid or a vitreous body in the posterior segment. The imaging target site may also be a peripheral site of the eye such as an eyelid or an orbit. Any known technique may be employed to form a cross sectional image or a three-dimensional image of the patient's eye based on the returning light of the OCT measurement light.

In this specification, images acquired by OCT may be collectively referred to as OCT images. Also, the measurement operation for forming OCT images may be referred to as OCT measurement. The contents of the document cited in the present specification can be appropriately incorporated as contents of the following embodiments.

In the following embodiments, a configuration to which Fourier domain OCT is employed will be described. In particular, with the ophthalmic operation microscope according to the embodiment, it is possible to acquire OCT images of a patient's eye by using a known swept source OCT technique. It is also possible to employ the configuration according to the present invention to an ophthalmic operation microscope using a type other than swept source OCT, for example, the technique of spectral domain OCT.

In the following embodiments, an apparatus in which an OCT optical system is employed to an ophthalmic operation microscope will be described. Note that it is also possible to employ the OCT optical system according to the embodiment to an ophthalmic observation apparatus other than an ophthalmic operation microscope, for example, to a scanning laser ophthalmoscope (SLO), a slit lamp microscope, a fundus camera, or the like.

In the present embodiment, directions such as up and down, right and left, front and rear, and the like are directions as viewed from the operator unless otherwise mentioned. With respect to the up and down directions, the direction from the objective lens 15 (to be described later)

toward the observation target (i.e., the patient's eye E) is defined as the down direction, and the opposite direction thereto is defined as the up direction. In general, a patient lies on his/her back during surgery. Therefore, the up and down direction and the vertical direction are the same.

[Exterior Configuration]

FIG. 1 shows an exterior configuration of an ophthalmic operation microscope according to the present embodiment. The ophthalmic operation microscope 1 includes the support 2, the first arm 3, the second arm 4, the driving device 5, the operator microscope 6, the assistant microscope 7, and the foot switch 8. The support 2 supports the entire ophthalmic operation microscope 1. One end of the first arm 3 is connected to the upper end of the support 2. One end of the second arm 4 is connected to the other end of the first arm 3. The driving device 5 is connected to the other end of the second arm 4. The operator microscope 6 is suspended by the driving device 5. The assistant microscope 7 is attached to the operator microscope 6. The foot switch 8 is used for performing various operations with feet of an operator or the like. The driving device 5 acts to three-dimensionally move the operator microscope 6 and the assistant microscope 7 in the vertical direction and the horizontal direction in accordance with the operation performed by an operator or the like.

The operator microscope 6 has the lens barrel unit 10 that houses various optical systems, various driving systems, and the like. On the upper portion of the lens barrel unit 10, the inverter unit 12 is provided. The inverter unit 12 includes a known optical unit (e.g., an image erecting prism) that converts an observation image obtained as an inverted image into an erect image. A pair of right and left eyepiece portions 11L and 11R are provided on the upper portion of the inverter unit 12. The operator looks in the eyepiece portions 11L and 11R and observes the patient's eye E with both eyes.

The front lens 13 is connected to the operator microscope 6 via the holding arm 14. The upper end portion of the holding arm 14 is pivotally provided so as to be rotatable in the vertical direction. The upper end portion of the holding arm 14 can retract the front lens 13 from the position between the patient's eye E and the front focal point of an objective lens (not shown). The retracted front lens 13 and the holding arm 14 are stored in a storage unit (not shown).

[Configuration of Optical System]

Figure 2:
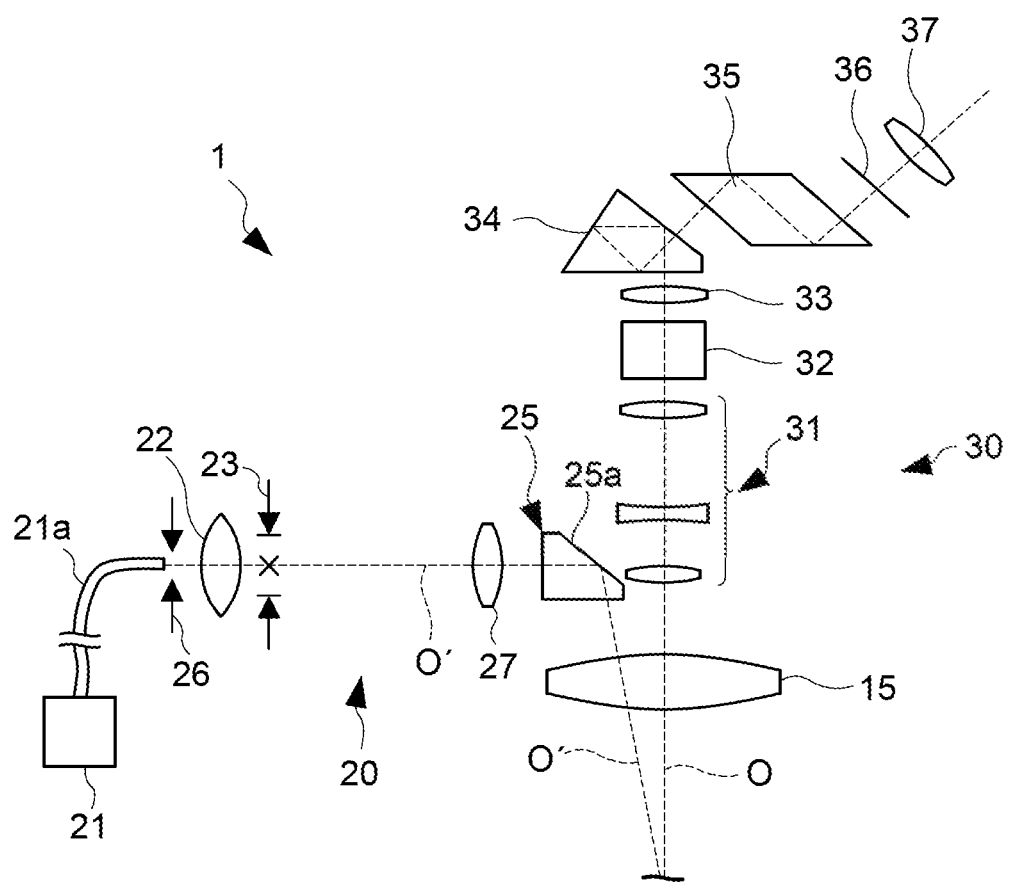
FIG. 2 is a schematic diagram illustrating an example of the configuration of an optical system of the ophthalmic operation microscope according to the embodiment.
Figure 3:
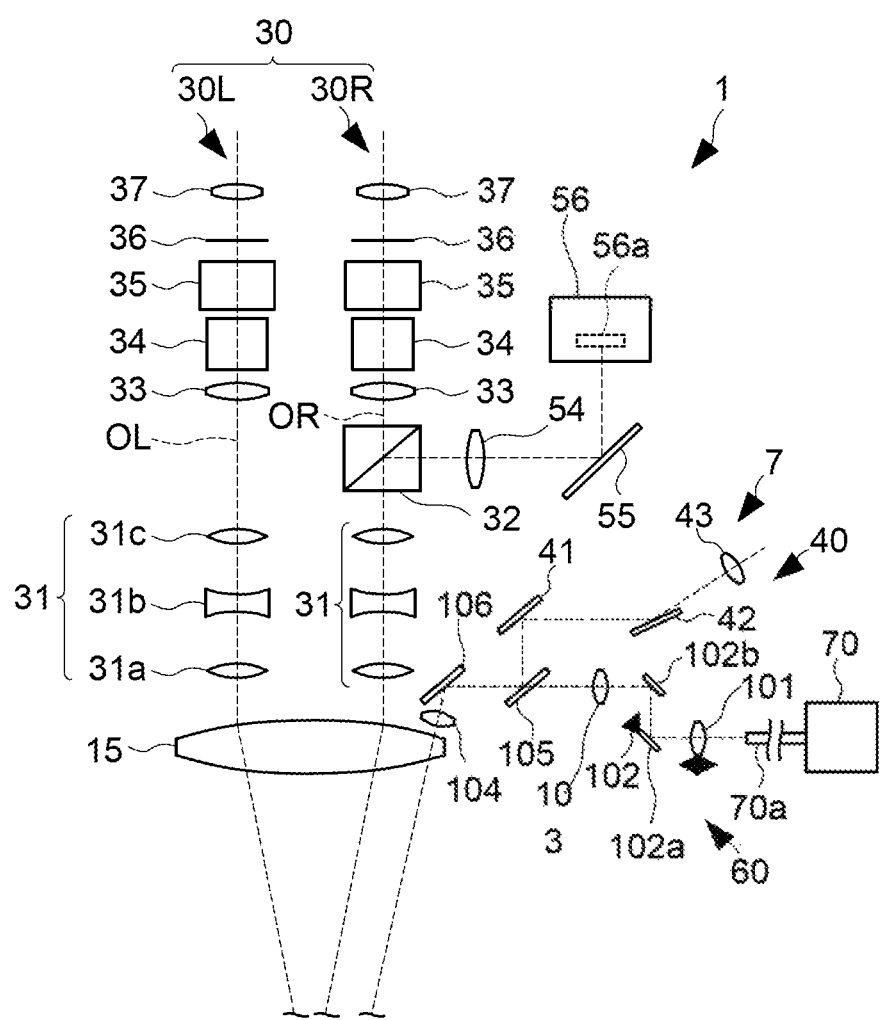
FIG. 3 is a schematic diagram illustrating an example of the configuration of an optical system of the ophthalmic operation microscope according to the embodiment.
Figure 4:
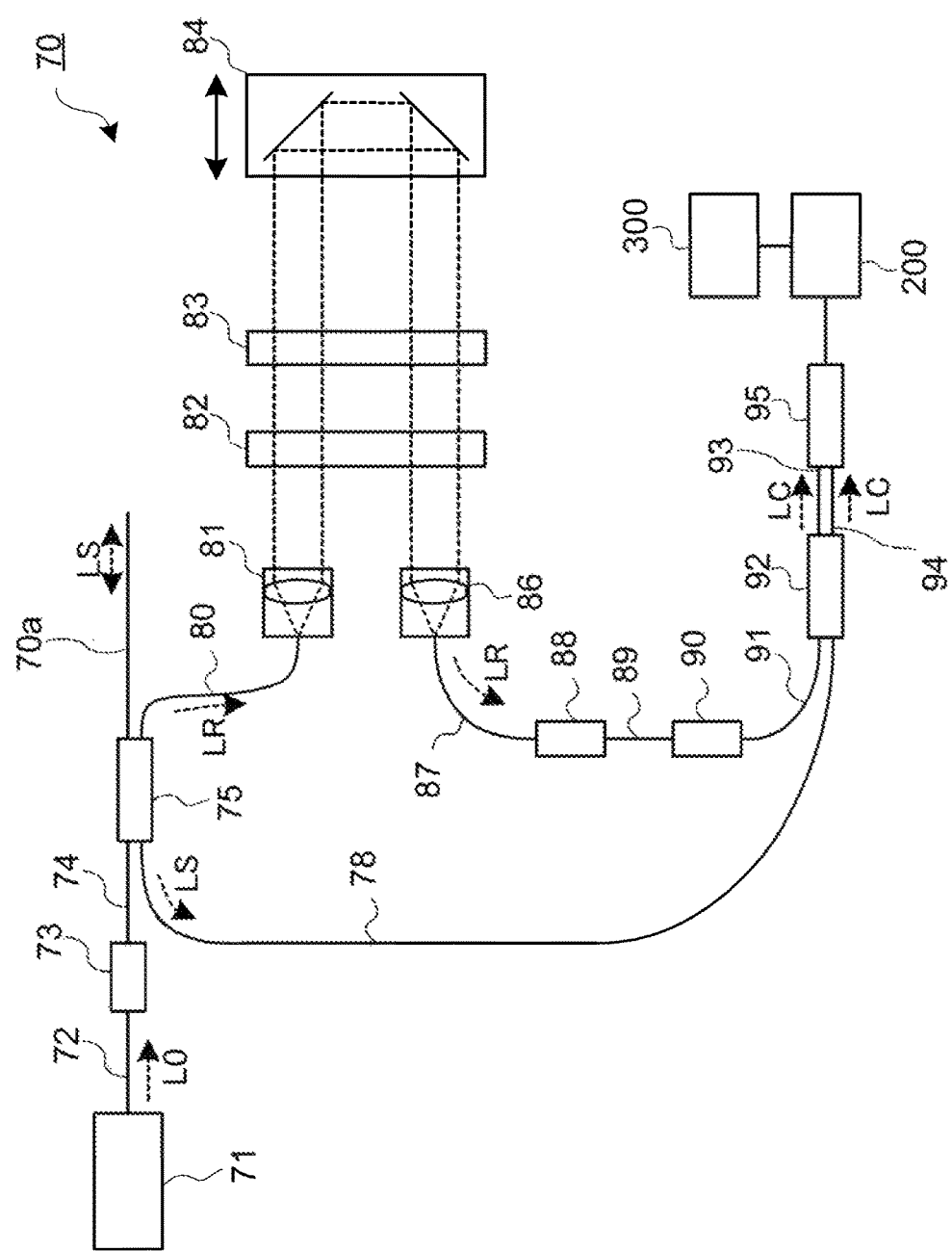
FIG. 4 is a schematic diagram illustrating an example of the configuration of an optical system of the ophthalmic operation microscope according to the embodiment.

FIG. 2 to FIG. 4 show examples of the configuration of the optical system of the ophthalmic operation microscope 1. FIG. 2 is a side view from the assistant microscope 7 side. FIG. 3 is a side view from the operator side. FIG. 4 shows a configuration example of the OCT unit 70 described later.

The optical system of the ophthalmic operation microscope 1 is housed in the lens barrel unit 10 of the operator microscope 6, and includes the objective lens 15, the illumination optical system 20, the main observation optical system 30, the secondary observation optical system 40, and the OCT optical system 60. The main observation optical system 30 is the optical system (i.e., the observation optical system) of the operator microscope 6, and the secondary observation optical system 40 is the optical system (i.e., the observation optical system) of the assistant microscope 7.

(Illumination Optical System)

The illumination optical system 20 illuminates the patient's eye E via the objective lens 15. As shown in FIG. 2, the illumination optical system 20 includes the illumination light source 21, the optical fiber 21a, the exit aperture diaphragm 26, the condenser lens 22, the illumination field diaphragm 23, the collimator lens 27, and the illumination prism 25.

The illumination field diaphragm 23 is provided at a position optically conjugate with the front focal position of the objective lens 15.

The illumination light source 21 is provided outside the lens barrel unit 10. One end of the optical fiber 21a is connected to the illumination light source 21. The other end of the optical fiber 21a is disposed at a position facing the condenser lens 22 in the lens barrel unit 10. The illumination light output from the illumination light source 21 is guided by the optical fiber 21a and enters the condenser lens 22.

The exit aperture diaphragm 26 is provided at a position facing the exit aperture of the optical fiber 21a (i.e., the fiber end on the condenser lens 22 side). The exit aperture diaphragm 26 acts to shield a partial region of the exit aperture of the optical fiber 21a. When the shielding region formed by the exit aperture diaphragm 26 is changed, the exit region of the illumination light is changed. Thereby, it is possible to change the illumination angle of the illumination light, that is, the angle between the incident direction of the illumination light with respect to the patient's eye E and the optical axis O of the objective lens 15.

The collimator lens 27 converts the illumination light that has passed through the illumination field diaphragm 23 into a parallel light beam. The illumination light that has become a parallel light beam is reflected by the reflection surface 25a of the illumination prism 25, passes through the objective lens 15, and is projected onto the patient's eye E. (Part of) the illumination light projected onto the patient's eye E is reflected by the cornea. The returning light (sometimes referred to as observation light) of the illumination light from the patient's eye E passes through the objective lens 15 and is incident on the main observation optical system 30 and the secondary observation optical system 40.

(Main Observation Optical System)

The main observation optical system 30 is used for observation of the patient's eye E being illuminated by the illumination optical system 20 with the operator microscope 6 via the objective lens 15. A pair of right and left main observation optical systems 30 are provided as shown in FIG. 3. The observation optical system 30L on the left is called the left observation optical system and the observation optical system 30R on the right is called the right observation optical system. The reference symbol OL indicates the optical axis (i.e., the observation optical axis) of the left observation optical system 30L, and the reference symbol OR indicates the optical axis (i.e., the observation optical axis) of the right observation optical system 30R. The left and right observation optical systems 30L and 30R are disposed so as to sandwich the optical axis O (see FIG. 2) of the objective lens 15. FIG. 3 illustrates the state in which the measurement light generated by the OCT optical system is incident on the patient's eye E at a predetermined incident angle; however, the configuration of the embodiment is not limited to the incident angle of the measurement light.

Each of the left and right observation optical systems 30L and 30R includes the zoom lens system 31, the beam splitter 32 (only in the right observation optical system 30R), the imaging lens 33, the image erecting prism 34, the eye width adjustment prism 35, the visual field diaphragm 36, and the eyepiece 37.

The zoom lens system 31 includes a plurality of zoom lenses 31a, 31b, and 31c. Each of the zoom lenses 31a to 31c is movable in a direction along the observation optical axis OL (or the observation optical axis OR) by a zooming mechanism (not shown). Thereby, the magnification upon observing or imaging the patient's eye E is changed.

The beam splitter 32 of the right observation optical system 30R splits part of the observation light guided along the observation optical axis OR from the patient's eye E and guides the part of the observation light to the imaging optical system. The imaging optical system includes the imaging lens 54, the reflection mirror 55, and the video camera 56.

The video camera 56 includes the image sensor 56a. The image sensor 56a is, for example, a charge coupled device (CCD) image sensor, a complementary metal oxide semiconductor (CMOS) image sensor, or the like. The image sensor 56a is an area sensor that has a two-dimensional light receiving surface.

When the ophthalmic operation microscope 1 is used, the light receiving surface of the image sensor 56a is disposed, for example, at a position optically conjugate with the surface of the cornea of the patient's eye E or at a position optically conjugate with the position away from the apex of the cornea by a half of the corneal curvature radius in the depth direction.

The image erecting prism 34 converts an inverted image into an erected image. The eye width adjustment prism 35 is an optical element for adjusting the distance between the right and left observation light according to the operator's eye width (i.e., the distance between the left eye and the right eye). The visual field diaphragm 36 shields the peripheral region in the cross section of the observation light to limit the field of view of the operator.

The main observation optical system 30 may include a stereo variator configured to be insertable into and removable from the optical path of the observation light. The stereo variator is an optical axis position changing element for changing the relative position between the observation optical axes OL and OR that are respectively guided by the left and right zoom lens system 31. By a solenoid controlled by the controller 210 which will be described later, the stereo variator is moved to be insertable into and removable from the observation optical path. For example, the stereo variator is retracted from the observation optical path to a retracted position provided on the operator side with respect to the observation optical path.

(Secondary Observation Optical System)

The secondary observation optical system 40 is used for observation of the patient's eye E being illuminated by the illumination optical system 20 with the assistant microscope 7 via the objective lens 15. The secondary observation optical system 40 guides the illumination light reflected by the patient's eye E illuminated by the illumination optical system 20 to the assistant eyepiece 43.

The secondary observation optical system 40 is also provided with a pair of right and left optical systems, enabling stereoscopic observation with both eyes. The position of the secondary observation optical system 40 can be changed relative to the main observation optical system 30 so that the assistant can change his/her position. In particular, the secondary observation optical system 40 is configured to be rotatable about the optical axis O of the objective lens 15.

The secondary observation optical system 40 includes the reflection mirrors 41 and 42 and the assistant eyepiece 43. The secondary observation optical system 40 may further include an imaging lens disposed between the objective lens 15 and the assistant eyepiece 43. In the present embodiment, the optical path of the secondary observation optical system 40 is disposed so as to overlap the optical path of the OCT optical system 60. The returning light of the illumination light from the patient's eye E travels through the optical path of the OCT optical system 60 (described later) and is reflected by the dichroic mirror 105 (described later). The returning light of the illumination light reflected by the dichroic mirror 105 is reflected by the reflection mirrors 41 and 42 and guided to the assistant eyepiece 43.

(OCT Optical System)

As shown in FIG. 3, the OCT optical system 60 includes the OCT unit 70, the optical fiber 70a, the collimator lens 101, the optical scanner 102, the first lens group 103, the second lens group 104, the dichroic mirror 105, and the deflection member 106.

As shown in FIG. 4, the OCT unit 70 includes an interference optical system. The interference optical system splits light emitted from the OCT light source unit 71 into the reference light LR and the measurement light LS and detects the interference light LC generated from the returning light of the measurement light LS guided to the patient's eye E and the reference light LR. One end of the optical fiber 70a is connected to the OCT unit 70. The measurement light LS generated by the interference optical system in the OCT unit 70 is emitted from the other end of the optical fiber 70a. The returning light of the measurement light LS guided to the patient's eye E by the OCT optical system 60 (described later) advances along the same path in the opposite direction and is incident on the other end of the optical fiber 70a.

The other end of the optical fiber 70a (i.e., the emitting end of the measurement light) is disposed at a position facing the collimator lens 101. The measurement light LS emitted from the other end of the optical fiber 70a is incident on the collimator lens 101. In addition, the returning light of the measurement light LS that has passed through the collimator lens 101 is incident on the other end of the optical fiber 70a.

The collimator lens 101 converts the measurement light LS emitted from the other end of the optical fiber 70a into a parallel light beam. The collimator lens 101 and the other end of the optical fiber 70a are configured to be relatively movable along the optical axis of the measurement light LS. In the present embodiment, the collimator lens 101 is configured to be movable along the optical axis of the measurement light LS, but the other end of the optical fiber 70a may be configured to be movable along the optical axis of the measurement light LS.

The optical scanner 102 deflects the measurement light LS, which has been made into a parallel light beam by the collimator lens 101, in a one-dimensional or two-dimensional manner. The optical scanner 102 includes a deflection member whose deflection surface is configured to be rotatable about one axis, or a deflection member whose deflection surface is configured to be rotatable about respective axes of two axes that are orthogonal to each other (or that are intersect with each other). Examples of the deflection member include a galvano mirror, a polygon mirror, a rotating mirror, a micro electro mechanical systems (MEMS) mirror scanner, and the like. In the present embodiment, the optical scanner 102 includes a galvano mirror. More specifically, the optical scanner 102 includes the first scanner 102a configured so that the deflection surface thereof is rotatable about a first axis, and the second scanner 102b configured so that the deflection surface thereof is rotatable about a second axis orthogonal to the first axis. A relay optical system may be provided between the first scanner 102a and the second scanner 102b.

The first lens group 103 includes one or more lenses. The second lens group 104 includes one or more lenses. The second lens group 104 is disposed in the vicinity position above the objective lens 15. The position (for example, the intermediate position) between the first scanner 102a and the second scanner 102b is substantially optically conjugate with the position on the surface of the objective lens 15 on the second lens group 104 side. The position between the first scanner 102a and the second scanner 102b includes the position in the deflection surface of the first scanner 102a or the second scanner 102b. It is possible to determine the magnification of the OCT optical system 60 based on the focal distance of the first lens group 103 and the focal distance of the second lens group 104.

Between the first lens group 103 and the second lens group 104, the dichroic mirror 105 and the deflection member 106 are disposed. The dichroic mirror 105 reflects visible light (e.g., the returning light of the illumination light) and transmits infrared light (e.g., the measurement light and its returning light). The returning light of the illumination light reflected by the dichroic mirror 105 is projected on the reflection mirror 41. The deflection member 106 deflects (reflects) the measurement light LS transmitted through the dichroic mirror 105 toward the objective lens 15 (i.e., toward the second lens group 104). In addition, the deflection member 106 deflects (reflects) the returning light of the illumination light and the returning light of the measurement light LS that have passed through the second lens group 104 toward the dichroic mirror 105. The dichroic mirror 105 may be a beam splitter or a half mirror. The deflection member 106 may be a total reflection mirror or a beam splitter (e.g., a half mirror or a dichroic mirror).

The second lens group 104 may be provided in the objective lens 15. The second lens group 104 may be provided on the surface of the objective lens 15 (for example, the surface on the side of the patient's eye E) or on the rear surface (for example, the surface on the side of the deflection member 106). A configuration may be employed in which a hole is formed in the objective lens 15 and the second lens group 104 and the deflection member 106 are disposed so that the returning light of the illumination light, the measurement light LS, and the returning light of the measurement light LS pass through the hole in the objective lens 15. Further, the second lens group 104 may be disposed in the vicinity position below the peripheral portion of the objective lens 15.

At least one of the first lens group 103 and the second lens group 104 may be configured to be movable along the optical axis of the measurement light LS instead of the movement of the collimator lens 101 in the optical axis direction. Alternatively, in addition to the movement of the collimator lens 101 in the optical axis direction, at least one of the first lens group 103 and the second lens group 104 may be configured to be movable along the optical axis of the measurement light LS.

The OCT optical system 60 is disposed, for example, so that the measurement light LS is incident from the side of the operator toward the central part of the objective lens 15. In the case where the main observation optical system 30 includes the stereo variator described above, one or more optical members among the optical members included in the OCT optical system 60 may be disposed at positions below the position of the stereo variator retracted from the observation optical path is disposed (i.e., below the retracted position). More specifically, at least part of the one or more optical members may be disposed so as to be included in a spatial region determined by extending the region occupied by the stereo variator disposed in the retracted position in the optical axis direction of the returning light of the illumination light. Such one or more optical members may include the second lens group 104. For example, the second lens group 104 and the deflection member 106 may be disposed below the retracted position of the stereo variator.

<OCT Unit>

The OCT unit 70 includes an interference optical system as shown in FIG. 4. The detection result (i.e., detection signal) of the interference light LC detected by the interference optical system is a signal indicating the spectrum of the interference light, and is sent to the arithmetic and control unit 200.

Like the general swept source OCT apparatus, the OCT light source unit 71 includes a wavelength scanning type (wavelength tunable type) light source capable of scanning (sweeping) the wavelength of outgoing light. The OCT light source unit 71 temporally changes the output wavelength in the near infrared wavelength band which cannot be visually recognized by the human eye. The light output from the OCT light source unit 71 is indicated by the reference symbol L0.

The light L0 output from the OCT light source unit 71 is guided to the polarization controller 73 by the optical fiber 72, and the polarization state of the light L0 is adjusted.

The polarization controller 73 adjusts the polarization state of the light L0 guided inside the optical fiber 72 by externally applying stress to the looped optical fiber 72, for example.

The light L0 whose polarization state has been adjusted by the polarization controller 73 is guided to the fiber coupler 75 through the optical fiber 74. The fiber coupler 75 splits the light L0 into the measurement light LS and the reference light LR.

The reference light LR is guided to the collimator 81 by the optical fiber 80 and converted into a parallel light beam. The reference light LR, which has become the parallel light beam, is guided to the corner cube 84 via the optical path length correction member 82 and the dispersion compensation member 83. The optical path length correction member 82 acts as a delay means for matching the optical path length (i.e., the optical distance) of the reference light LR and that of the measurement light LS. The dispersion compensation member 83 acts as a dispersion compensation means for matching the dispersion characteristic of the reference light LR and that of the measurement light LS.

The corner cube 84 changes the traveling direction of the reference light LR that has been made into the parallel light beam by the collimator 81 in the opposite direction. The optical path of the reference light LR incident on the corner cube 84 and the optical path of the reference light LR emitted from the corner cube 84 are parallel. Further, the corner cube 84 is movable in a direction along the incident optical path and the emitting optical path of the reference light LR. Through such movement, the length of the optical path of the reference light LR (i.e., the reference optical path) is varied.

The reference light LR that has traveled through the corner cube 84 travels through the dispersion compensation member 83 and the optical path length correction member 82, is converted from the parallel light beam into a convergent light beam by the collimator 86, enters the optical fiber 87, is guided to the polarization controller 88. Then, the polarization state of the reference light LR is adjusted by the polarization controller 88.

The polarization controller 88 has a configuration similar to, for example, the polarization controller 73. The reference light LR whose polarization state has been adjusted by the polarization controller 88 is guided to the attenuator 90 by the optical fiber 89, and the light amount of the reference light LR is adjusted under the control of the arithmetic and control unit 200. The reference light LR whose light amount has been adjusted by the attenuator 90 is guided to the fiber coupler 92 by the optical fiber 91.

The measurement light LS generated by the fiber coupler 75 is guided to the collimator lens 101 by the optical fiber 70a (see FIG. 3). The measurement light LS that has entered the collimator lens 101 reaches the deflection member 106 via the optical scanner 102, the first lens group 103, and the dichroic mirror 105. Then, the measurement light LS is reflected by the deflection member 106 and is projected onto the patient's eye E via the second lens group 104 and the objective lens 15. The measurement light LS is scattered (and reflected) at various depth positions of the patient's eye E. The backscattered light of the measurement light LS generated by the patient's eye E advances in the same path as the forward path in the opposite direction and is led to the fiber coupler 75, and then reaches the fiber coupler 92 via the optical fiber 78.

The fiber coupler 92 generates the interference light by superposing the measurement light LS incident through the optical fiber 78 and the reference light LR incident through the optical fiber 91 with each other (i.e., by making the measurement light LS incident through the optical fiber 78 and the reference light LR incident through the optical fiber 91 interfere with each other). The fiber coupler 92 generates a pair of interference lights LC by splitting the interference light generated from the measurement light LS and the reference light LR at a predetermined branching ratio (for example, 50:50). The pair of interference light LC emitted from the fiber coupler 92 is guided to the detector 95 by the optical fibers 93 and 94, respectively.

The detector 95 is, for example, a balanced photo diode (hereinafter referred to as BPD) which includes a pair of photodetectors that respectively detect a pair of interference lights LC and outputs the difference between the detection results obtained by the photodetectors. The detector 95 sends a detection result (i.e., a detection signal) to the arithmetic and control unit 200. For example, the arithmetic and control unit 200 forms a cross sectional image by applying Fourier transform and so forth to the spectral distribution generated based on the detection results obtained by the detector 95 for each series of wavelength scans (i.e., for each A line). The arithmetic and control unit 200 causes the display unit 300 to display the formed image.

In the present embodiment, a Michelson interferometer is employed. However, any type of interferometer such as a Mach-Zehnder type or the like can be applied as appropriate.

[Arithmetic and Control Unit]

The configuration of the arithmetic and control unit 200 will be described. The arithmetic and control unit 200 analyzes the detection signals input from the detector 95 to form an OCT image of the patient's eye E. The arithmetic processing for the OCT image formation is performed in the same manner as in the conventional swept source OCT apparatus.

Further, the arithmetic and control unit 200 controls the OCT optical system 60. For example, the arithmetic and control unit 200 causes the display unit 300 to display the OCT image of the patient's eye E. As a control on the OCT optical system 60, the arithmetic and control unit 200 executes the operation control of the OCT light source unit 71, the movement control of the corner cube 84, the operation control of the detector 95, the operation control of the attenuator 90, the operation control of the polarization controllers 73 and 88, and the like. In addition, the arithmetic and control unit 200 can perform the focus control by moving the collimator lens 101, the first lens group 103, and the second lens group 104 in the optical axis direction, the scan control by the optical scanner 102, and the like.

Like the conventional computer, the arithmetic and control unit 200 includes, for example, a microprocessor, a random access memory (RAM), a read only memory (ROM), a hard disk drive, a communication interface, and the like. A computer program for controlling the ophthalmic operation microscope 1 is stored in a storage device such as the hard disk drive. The arithmetic and control unit 200 may include various kinds of circuitry, for example, a circuit board for the OCT image formation. In addition, the arithmetic and control unit 200 may include a display device such as a liquid crystal display (LCD), an operation device (an input device) such as a keyboard and a mouse, or the like.

[Control System]

Figure 5:
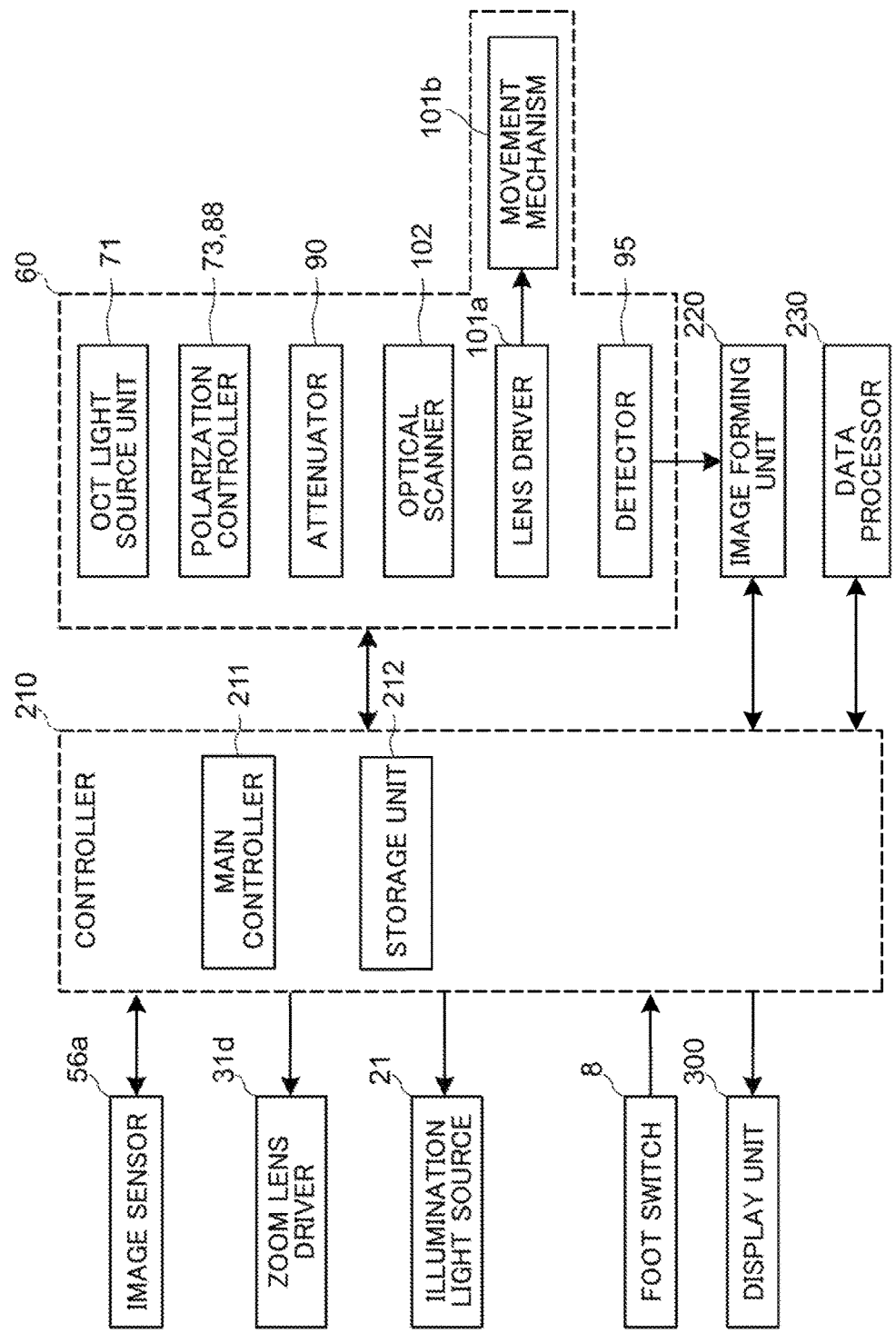
FIG. 5 is a schematic diagram illustrating an example of the configuration of a control system of the ophthalmic operation microscope according to the embodiment.

FIG. 5 shows an example of the configuration of the control system of the ophthalmic operation microscope 1. In FIG. 5, parts similar to those in FIGS. 1 to 4 are denoted by the same reference symbols, and description thereof is omitted as appropriate.

(Controller)

The controller 210 is the center of the control system of the ophthalmic operation microscope 1. The controller 210 has functions of both a control means for controlling the ophthalmic operation microscope 1 and a control means (the arithmetic and control unit 200) for controlling the OCT optical system 60. One or more elements for realizing these means may be distributed between the inside and the outside of the ophthalmic operation microscope 1. The controller 210 includes, for example, the aforementioned microprocessor, RAM, ROM, hard disk drive, communication interface, and the like. The controller 210 is provided with the main controller 211 and the storage unit 212.

(Main Controller)

The main controller 211 performs the various kinds of controls described above. In particular, the main controller 211 controls the image sensor 56a, the zoom lens driver 31d, and the illumination light source 21 of the ophthalmic operation microscope 1. Further, the main controller 211 controls the OCT light source unit 71, the polarization controllers 73 and 88, the attenuator 90, the lens driver 101a, the optical scanner 102, the detector 95, the image forming unit 220, and the data processor 230. For example, the main controller 211 can perform the various kinds of controls described above based on the contents of an operation performed using the foot switch 8 input by the operator.

The zoom lens driver 31d moves each of the zoom lenses 31a, 31b and 31c included in the zoom lens system 31 in a direction along the observation optical axis OL (or the observation optical axis OR) in an independent manner.

The lens driver 101a controls the movement mechanism 101b. The movement mechanism 101b moves the collimator lens 101 along the optical axis of the measurement light LS. For example, the movement mechanism 101b includes a holding member configured to hold the collimator lens 101, a sliding mechanism configured to move the holding member in the direction of the optical axis of the measurement light LS, and a member configured to transmit the driving force generated by the lens driver 101a to the sliding mechanism. The main controller 211 can move the collimator lens 101 by controlling the lens driver 101a so that the intensity of the returning light of the measurement light LS from the patient's eye E, the intensity of the interference light LC, and/or the intensity of the detection signal becomes equal to or higher than a predetermined intensity, for example. Further, the movement mechanism 101b can move the collimator lens 101 manually. In the case of manual moving, the movement mechanism 101b can move the collimator lens 101 by controlling the lens driver 101a based on the content of an operation performed using the foot switch 8 or an operation unit (not shown) by the user (for example, by the operator).

The movement mechanism 101b may be configured to move at least one of the first lens group 103 and the second lens group 104 along the optical axis of the measurement light LS. In this case, the main controller 211 can move the at least one of the first lens group 103 and the second lens group 104 along the optical axis of the measurement light LS by controlling the lens driver 101a.

In addition, the main controller 211 performs a process of writing data to the storage unit 212 and a process of reading out data from the storage unit 212.

(Image Forming Unit)

Based on the detection signals from the detector 95, the image forming unit 220 forms image data of a cross sectional image of the anterior segment, the fundus, or the like. The image forming processing includes processes such as noise removal (noise reduction), filter processing, and fast Fourier transform (FFT) in the same manner as the conventional swept source OCT. In the case of employing an OCT apparatus of another type, the image forming unit 220 performs known processing according to the type employed.

(Data Processor)

The data processor 230 performs various kinds of image processing and various kinds of analysis processing on the image formed by the image forming unit 220. For example, the data processor 230 performs various kinds of correction processes such as brightness correction, dispersion correction, and the like on the image. In addition, the data processor 230 can also apply various kinds of image processing and various kinds of analysis processing to the image (e.g., the fundus image, the anterior segment image, or the like) obtained by the ophthalmic operation microscope 1.

The data processor 230 performs known image processing such as interpolation processing for interpolating pixels between cross sectional images to form image data of a three-dimensional image of the anterior segment, the fundus, or the like. Note that image data of a three-dimensional image means image data in which the position of a pixel is defined by a three-dimensional coordinate system. Examples of the image data of the three-dimensional image include image data defined by voxels three-dimensionally arranged. This image data is called volume data or voxel data. When an image based on the volume data is to be displayed, the data processor 230 performs a rendering process on the volume data to form image data of a pseudo three-dimensional image when viewed from a specific line-of-sight direction. Examples of the rendering process include volume rendering, maximum intensity projection (MIP), and the like. The pseudo three-dimensional image is displayed on a display device such as the display unit 300.

In addition, it is also possible to form stack data of a plurality of cross sectional images as the image data of the three-dimensional image. The stack data is image data obtained by arranging a plurality of cross sectional images obtained along a plurality of scanning lines in a three-dimensional manner based on the positional relationship of the scanning lines. In other words, the stack data is image data obtained by representing a plurality of cross sectional images, which are originally defined by individual two-dimensional coordinate systems, by a single three-dimensional coordinate system (that is, the stack data is image data obtained by embedding a plurality of cross sectional images in a single three-dimensional space).

The data processor 230 functioning as described above includes, for example, the aforementioned microprocessor, RAM, ROM, hard disk drive, circuitry, and the like. In a storage device such as the hard disk drive, a computer program for causing the microprocessor to execute the functions described above is stored in advance.

In the present embodiment, the interference optical system includes the fiber couplers 75 and 92, the detector 95, and optical fibers and/or various kinds of optical members for guiding the reference light LR and/or the measurement light LS therebetween. The interference optical system may further include the OCT light source unit 71. The interference optical system thus configured is an example of the "interference optical system" in the present embodiment. The main observation optical system 30 is an example of the "observation optical system" according to the present embodiment. The dichroic mirror 105 is an example of the "optical path coupling member" according to the present embodiment. The movement mechanism 101b is an example of the "first movement mechanism" and the "second movement mechanism" according to the present embodiment. The secondary observation optical system 40 is an example of the "another optical system" according to the present embodiment, which performs at least one of projecting light onto the patient's eye and receiving light from the patient's eye.

Operation Example

An example of the operation of the ophthalmic operation microscope 1 having the above configuration will be described.

First, adjustment of the observation state using the ophthalmic operation microscope 1 is performed. For the ophthalmic operation microscope 1 to do so, for example, the operator performs adjustments of the ophthalmic operation microscope 1. That is, after adjusting the position and the orientation of the second arm 4, the operator performs an operation using the foot switch 8 to move the operator microscope 6 and the assistant microscope 7 in the vertical direction and the horizontal direction, and stops the operator microscope 6 and the assistant microscope 7 at a desired position. After that, the operator adjusts the eye width, the observation angle, the light amount, and so forth, and adjusts the focus and the position. This makes the patient's eye E to be illuminated by the illumination light projected by the illumination optical system 20. As a result, the operator can observe the patient's eye E while looking through the eyepiece 37 and the assistant can observe the patient's eye E while looking through the assistant eyepiece 43.

When OCT measurement is performed, the scan area and the scan pattern (e.g., the shape of the scan area, the size of the scan area, and the like) of the measurement light for the OCT measurement are set. The scan area of the measurement light can be set automatically or manually. In the case of automatically setting the scan area of the measurement light, for example, it is possible to set the scan area by reproducing the same area as the preoperative OCT measurement. In addition, it is also possible to automatically set the scan area by analyzing a frame of the current observation image acquired by the TV camera 56 to detect a surgical target site, and by setting the area that includes the detected surgical target site as the scan area. The area of the preoperative OCT measurement can be specified by recording the preoperative OCT scan area in the three-dimensional image or the front image and comparing it with a frame of the current observation image. On the other hand, in the case of manually setting the scan area of the measurement light, for example, the operator sets a desired scan area while watching the live image of the OCT image. Examples of the method of setting the scan pattern include automatic setting of the same scan pattern as before surgery and manual setting using the foot switch 8. In the case of manually setting the scan pattern, options of the scan pattern are presented on the display unit 300 or the like, and a desired option is designated by the use of the foot switch 8 or the like. The options of the scan pattern may include at least one of a one-dimensional pattern and a two-dimensional pattern.

After completing the setting related to the scan of the measurement light, the OCT measurement is started. Note that, in the case where the live image of the OCT image is used for the setting, the OCT measurement has already been started. In order to perform OCT measurement, the controller 210 controls the OCT light source unit 71, the corner cube 84, and the like, and also controls the optical scanner 102 based on the scan area set as described above. The image forming unit 220 forms a cross sectional image of the patient's eye E based on the spectrum of the interference light obtained through the OCT measurement. When the scan pattern is the three-dimensional scan, the data processor 230 forms a three-dimensional image of the patient's eye E based on the plurality of cross sectional images formed by the image forming unit 220.

The operator can perform surgery while selectively performing visual observation with the ophthalmic operation microscope 1, observation of a visible image acquired by the ophthalmic operation microscope 1, and observation of OCT image acquired by the OCT optical system 60.

[First Modification Example]

At least one of the optical members included in the OCT optical system 60 may be configured as a unit (i.e., an attachment) attachable to and detachable from the lens barrel unit 10 (or the main body of the microscope). Such an attachable and detachable unit includes one or more optical members including the first lens group 103.

The attachable and detachable unit may be configured, for example, as being integrated with the secondary observation optical system 40 of the assistant microscope 7. For example, the second lens group 104 and the deflection member 106 are stored in the lens barrel unit 10. The attachable and detachable unit includes the reflection mirrors 41 and 42, the assistant eyepiece 43, the collimator lens 101, the optical scanner 102, and the first lens group 103. In addition, the attachable and detachable unit is connected to the OCT unit 70 via the optical fiber 70a. The attachable and detachable unit may further include the OCT unit 70.

Further, the attachable and detachable unit may be configured to be attachable to and detachable from the assistant microscope 7, for example. In this case, the attachable and detachable unit includes the collimator lens 101, the optical scanner 102, and the first lens group 103. In addition, the attachable and detachable unit is connected to the OCT unit 70 via the optical fiber 70a. The attachable and detachable unit may further include the OCT unit 70.

[Second Modification]

In the aforementioned embodiment, the case has been described in which the optical path of the OCT optical system 60 is coupled to the optical path of the secondary observation optical system 40. However, the configuration of the ophthalmic operation microscope according to the embodiment is not limited thereto. For example, a configuration may be employed in which the optical path of the OCT optical system 60 is coupled to the optical path of the illumination optical system 20 or to the optical path of the main observation optical system 30.

A configuration may be employed in which the optical path of the OCT optical system 60 is directly guided to the objective lens 15 without being coupled to the optical path of the illumination optical system 20, the optical path of the main observation optical system 30, or the optical path of the secondary observation optical system 40.

Further, the optical path of the OCT optical system 60 may be coupled to the optical path of an optical system other than the optical systems described in the above embodiment. For example, the optical path of the OCT optical system 60 may be coupled to the optical path of an imaging optical system that guides the observation light to an image sensor, the optical path of an OCT optical system separately provided from the OCT optical system 60, the optical path of a laser projection optical system that projects a laser beam onto the patient's eye, or the optical path of a sensor optical system that includes a wavefront sensor or the like. A configuration may be employed in which the optical path of the OCT optical system 60 is coupled to the optical path of an optical system other than the optical systems described above.

[Effects]

The effects of the ophthalmic operation microscope according to the embodiment will be described.

The ophthalmic operation microscope (e.g., the ophthalmic operation microscope 1) according to the embodiment includes an illumination optical system, an observation optical system, an objective lens, an interference optical system (e.g., the fiber couplers 75 and 92, the detector 95, etc.), a first lens group, a second lens group, and a deflection member. The illumination optical system (e.g., the illumination optical system 20) is configured to illuminate a patient's eye (e.g., the patient's eye E) with illumination light. The observation optical system (e.g., the main observation optical system 30) is used for observing the patient's eye illuminated by the illumination optical system. The objective lens (e.g., the objective lens 15) is disposed in an observation optical path. The interference optical system is configured to split light from a light source (e.g., the OCT light source unit 71) into measurement light (e.g., the measurement light LS) and reference light (e.g., the reference light LR) and detect interference light (e.g., the interference light LC) generated from returning light of the measurement light from the patient's eye (e.g., the patient's eye E) and the reference light. The first lens group (e.g., the first lens group 103) is disposed between the light source and the patient's eye in an optical path of the measurement light. The second lens group (e.g., the second lens group 104) is disposed between the first lens group and the patient's eye in the optical path of the measurement light. The deflection member (e.g., the deflection member 106) is disposed between the first lens group and the second lens group in the optical path of the measurement light.

According to such a configuration, since the deflection member is disposed between the first lens group and the second lens group, the measurement light from the interference optical system that has passed through the first lens group can be deflected. With this, an optical system for guiding the measurement light to the patient's eye can be disposed without protruding from the main body of the microscope. Therefore, it is possible to reduce the size of the ophthalmic operation microscope used for observing the patient's eye and acquiring OCT images.

Also, in the ophthalmic operation microscope according to the embodiment, the deflection member may be configured to reflect the measurement light having passed through the first lens group toward the patient's eye.

According to such a configuration, it is possible to use the deflection member that reflects the measurement light. This makes it possible to further reduce the size and the cost of the ophthalmic operation microscope.

In addition, the ophthalmic operation microscope according to the embodiment may include an optical scanner (e.g., the optical scanner 102). The optical scanner is disposed between the light source and the first lens group in the optical path of the measurement light.

According to such a configuration, it becomes possible to scan the patient's eye with the measurement light in order to acquire OCT images while observing the patient's eye.

In addition, in the ophthalmic operation microscope according to the embodiment, the optical scanner may include a first scanner (e.g., the first scanner 102a) and a second scanner (e.g., the second scanner 102b) having mutually different deflection directions. A position between the first scanner and the second scanner and a position on a surface of the objective lens on the second lens group side are substantially optically conjugate with each other.

According to such a configuration, it is possible to acquire an OCT image of the patient's eye with high image quality.

In addition, the ophthalmic operation microscope according to the embodiment may further include a collimator lens (e.g., the collimator lens 101). The collimator lens is disposed between the light source and the optical scanner in the optical path of the measurement light.

According to such a configuration, it is possible to scan the patient's eye with the measurement light that has been made into a parallel light beam.

In addition, in the ophthalmic operation microscope according to the embodiment, an emitting end of an optical fiber (e.g., the optical fiber 70a) that guides the measurement light generated by the interference optical system is disposed at a position facing the collimator lens.

According to such a configuration, the measurement light can be guided by the optical fiber without being restricted by the position at which the collimator lens is disposed.

This leads to an increase of the degree of freedom in the position at which the interference optical system is to be disposed.

In addition, the ophthalmic operation microscope according to the embodiment includes a first movement mechanism (e.g., the movement mechanism 101b). The first movement mechanism is configured to relatively move the collimator lens and the emitting end along an optical axis of the measurement light.

According to such a configuration, it is possible to perform focus adjustment of the measurement light through the movement of the collimator lens. This makes it possible to provide an ophthalmic operation microscope capable of acquiring OCT images with a simple configuration and control.

In addition, the ophthalmic operation microscope according to the embodiment further includes a second movement mechanism (e.g., the movement mechanism 101b). The second movement mechanism is configured to move at least one of the first lens group and the second lens group along the optical axis of the measurement light.

According to such a configuration, it is possible to perform focus adjustment of the measurement light through the movement of at least one of the first lens group and the second lens group. Therefore, it is possible to provide an ophthalmic operation microscope capable of acquiring OCT images with a simple configuration and control.

The ophthalmic operation microscope according to the embodiment further includes an optical path coupling member (e.g., the dichroic mirror 105). The optical path coupling member is configured to couple the optical path of the measurement light to an optical path of another optical system that performs at least one of the projection of light onto the patient's eye and the reception of light from the patient's eye. The secondary observation optical system 40 is an example of the another optical system.

According to such a configuration, the optical path of the measurement light and the optical path of the secondary optical system can be disposed over one another with respect to the objective lens. Therefore, the extensibility of the ophthalmic operation microscope can be increased. For example, it is possible to provide another optical system separately.

Further, in the ophthalmic operation microscope according to the embodiment, one or more members including the first lens group may be configured as a unit attachable to and detachable from a main body of the microscope.

According to such a configuration, the unit that includes an optical member(s) for acquiring OCT images can be attached to and detached from the main body of the microscope, as necessary.

[Other Modification Examples]

The above-described embodiment is merely an example for carrying out the present invention. Those who intend to implement the present invention can apply any modification, omission, addition, or the like within the scope of the gist of the present invention.

In the embodiment described above, the deflection member 106 may include an optical member having at least a function of changing the traveling direction of light, such as a non-planar mirror (e.g., a concave mirror), a deflection prism, or a diffraction grating.

It is possible to combine the configurations described in the above embodiments in an arbitrary manner.

The invention claimed is:

1. An ophthalmic operation microscope comprising:
    an illumination optical system configured to illuminate a patient's eye with illumination light;
    an observation optical system configured for observing the patient's eye illuminated by the illumination optical system;
    an objective lens disposed in an observation optical path;
    an interference optical system configured to split light from a light source into measurement light and reference light, project the measurement light to the patient's eye so that the measurement light is incident from a direction deviated from an optical axis of the observation optical system toward a central part of the objective lens, and detect interference light generated from returning light of the measurement light from the patient's eye and the reference light;
    a first lens group disposed between the light source and the patient's eye in an optical path of the measurement light;
    a second lens group disposed between the first lens group and the patient's eye in the optical path of the measurement light; and
    a deflection member disposed between the first lens group and the second lens group in the optical path of the measurement light.

2. The ophthalmic operation microscope of claim 1, wherein the deflection member reflects the measurement light having passed through the first lens group toward the patient's eye.

3. The ophthalmic operation microscope of claim 1, further comprising an optical scanner disposed between the light source and the first lens group in the optical path of the measurement light.

4. The ophthalmic operation microscope of claim 3, wherein
the optical scanner comprises a first scanner and a second scanner having mutually different deflection directions, and
a position between the first scanner and the second scanner and a position on a surface of the objective lens on the second lens group side are substantially optically conjugate with each other.

5. The ophthalmic operation microscope of claim 3, further comprising a collimator lens disposed between the light source and the optical scanner in the optical path of the measurement light.

6. The ophthalmic operation microscope of claim 5, wherein an emitting end of an optical fiber that guides the measurement light generated by the interference optical system is disposed at a position facing the collimator lens.

7. The ophthalmic operation microscope of claim 6, further comprising a first movement mechanism configured to relatively move the collimator lens and the emitting end along an optical axis of the measurement light.

8. The ophthalmic operation microscope of claim 1, further comprising a second movement mechanism configured to move at least one of the first lens group and the second lens group along an optical axis of the measurement light.

9. The ophthalmic operation microscope of claim 1, further comprising an optical path coupling member configured to couple the optical path of the measurement light to an optical path of another optical system that performs at least one of projecting light onto the patient's eye and receiving light from the patient's eye.

10. The ophthalmic operation microscope of claim 1, wherein one or more members comprising the first lens group are configured as a unit attachable to and detachable from a main body of the microscope.

\* \* \* \* \*